US008019089B2

(12) United States Patent
Seltzer et al.

(10) Patent No.: US 8,019,089 B2

(45) Date of Patent: Sep. 13, 2011

(54) REMOVAL OF NOISE, CORRESPONDING TO USER INPUT DEVICES FROM AN AUDIO SIGNAL

(75) Inventors: Michael Seltzer, Seattle, WA (US); Alejandro Acero, Bellevue, WA (US); Amarnag Subramanya, Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 1273 days.

(21) Appl. No.: 11/601,959

(22) Filed: Nov. 20, 2006

(65) Prior Publication Data

US 2008/0118082 A1 May 22, 2008

(51) Int. Cl.
*A61F 11/06* (2006.01)

(52) U.S. Cl. ......... 381/71.1; 381/94.1; 704/233; 700/94

(58) Field of Classification Search ................. 381/71.1, 381/94.1, 94.2, 94.3, 317; 704/226, 227, 704/228, 233; 700/94; 379/421
See application file for complete search history.

(56) References Cited

U.S. PATENT DOCUMENTS

| | | | | |
|---|---|---|---|---|
| 6,581,032 | B1 * | 6/2003 | Gao et al. | 704/222 |
| 7,020,605 | B2 * | 3/2006 | Gao | 704/225 |
| 2004/0001599 | A1 * | 1/2004 | Etter et al. | 381/94.1 |
| 2005/0114124 | A1 * | 5/2005 | Liu et al. | 704/228 |

* cited by examiner

*Primary Examiner* — Vivian Chin
*Assistant Examiner* — Friedrich W Fahnert
(74) *Attorney, Agent, or Firm* — Westman Champlin & Kelly P.A.

(57) ABSTRACT

A noisy audio signal, with user input device noise, is received. Particular frames in the audio signal that are corrupted by user input device noise are identified and removed. The removed audio data is then reconstructed to obtain a clean audio signal.

19 Claims, 7 Drawing Sheets

FIG. 6A
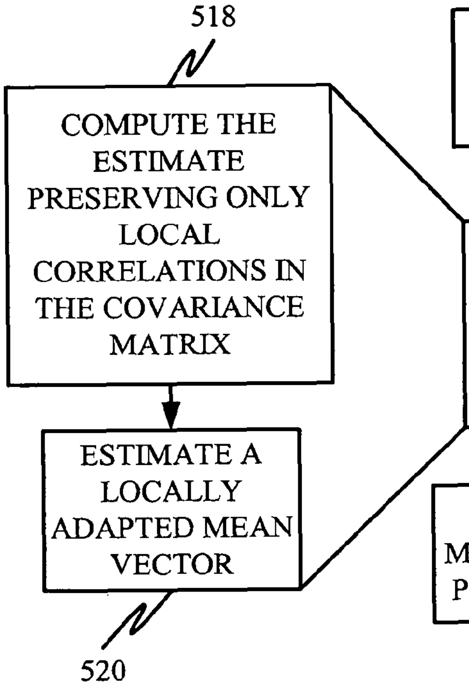
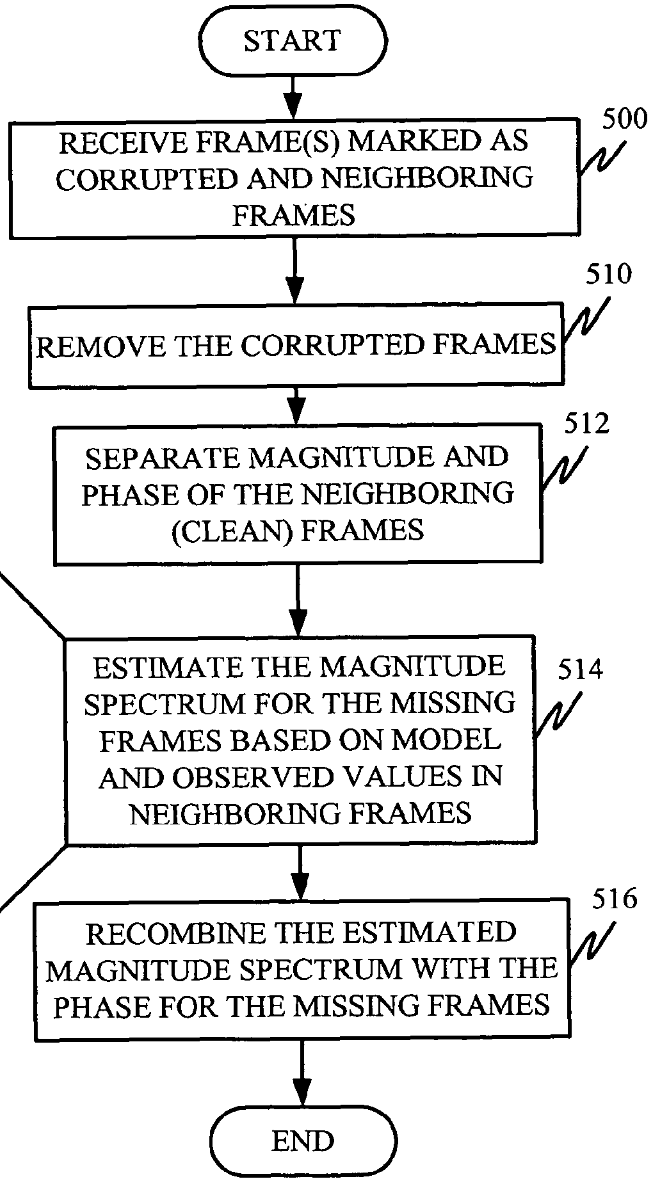
FIG. 6

REMOVAL OF NOISE, CORRESPONDING TO USER INPUT DEVICES FROM AN AUDIO SIGNAL

BACKGROUND

Personal computers and laptop computers are increasingly being used as devices for sound capture in a variety of recording and communication scenarios. Some of these scenarios includes recording of meetings and lectures for archival purposes, and the transmission of voice data for voice over IP (VOIP) telephony, video conferencing and audio/video instant messaging. In these types of scenarios, recording is typically done using the local microphone for the particular computer being used. This recording configuration is highly vulnerable to environmental noise sources. In particular, this configuration is particularly vulnerable to a specific type of additive noise, that of a user simultaneously using a user input device, such as typing on the keyboard of the computer being used for sound capture, mouse clicks or even stylus taps, to name a few.

There are many reasons that a user may be using a keyboard or other input device during sound capture. For instance, while recording a meeting, the user may often take notes on the same computer. Similarly, when video conferencing, users often multi-task while talking to another party, by typing emails or notes, or by navigating and browsing the web for information. In these types of situations, the keyboard or other user input device may commonly be closer to the microphone than the speaker. Therefore, the speech signal can be significantly corrupted by the sound of the user's input activity, such as keystrokes.

Continuous typing on a keyboard, mouse clicks, or stylus taps, for instance, produce a sequence of noise-like impulses in the audio stream. The presence of this nonstationary, impulsive noise in the captured speech can be very unpleasant for the listener.

In the past, some attempts have been made to deal with impulsive noise related to keystrokes. However, these have typically included an attempt to explicitly model the keystroke noise. This presents significant problems, however, because keystroke noise (and other user input noise, for that matter) can be highly variable across different users and across different keyboard devices.

The discussion above is merely provided for general background information and is not intended to be used as an aid in determining the scope of the claimed subject matter.

SUMMARY

A noisy audio signal, with user input device noise, is received. Particular frames in the audio signal that are corrupted by the user input device noise are identified and removed. The removed audio frames are then reconstructed to obtain a clean audio signal.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 6 is a flow diagram illustrating one embodiment of the reconstruction of corrupted frames.

DETAILED DESCRIPTION

The present invention can be used to detect and remove noise associated with physical manipulation of many types of user input devices from an audio stream. Some such user input devices include keyboards, computer mice, touch screen devices that are used with a stylus, to name but a few examples. The invention will be described herein in terms of keystroke noise, but that is not intended to limit the invention in any way and is exemplary only.

Keys on conventional keyboards are mechanical pushbutton switches. Therefore, a typed keystroke appears in an audio signal as two closely spaced noise-like impulses, one generated by the key-down action and the other by the key-up action. The duration of a keystroke is typically between 60-80 ms but may last up to 200 ms. Keystrokes can be broadly classified as spectrally flat. However, the inherent variety of typing styles, key sequences, and the mechanics of the keys themselves, introduce a degree of randomness in the spectral content of a keystroke. This leads to a significant variability across frequency and time for even the same key. It has also been empirically found that the keystroke noise primarily affects only the magnitude of an audio signal (e.g., a speech signal) and has virtually no human perceptual affect on the phase of the signal.

Figure 1:
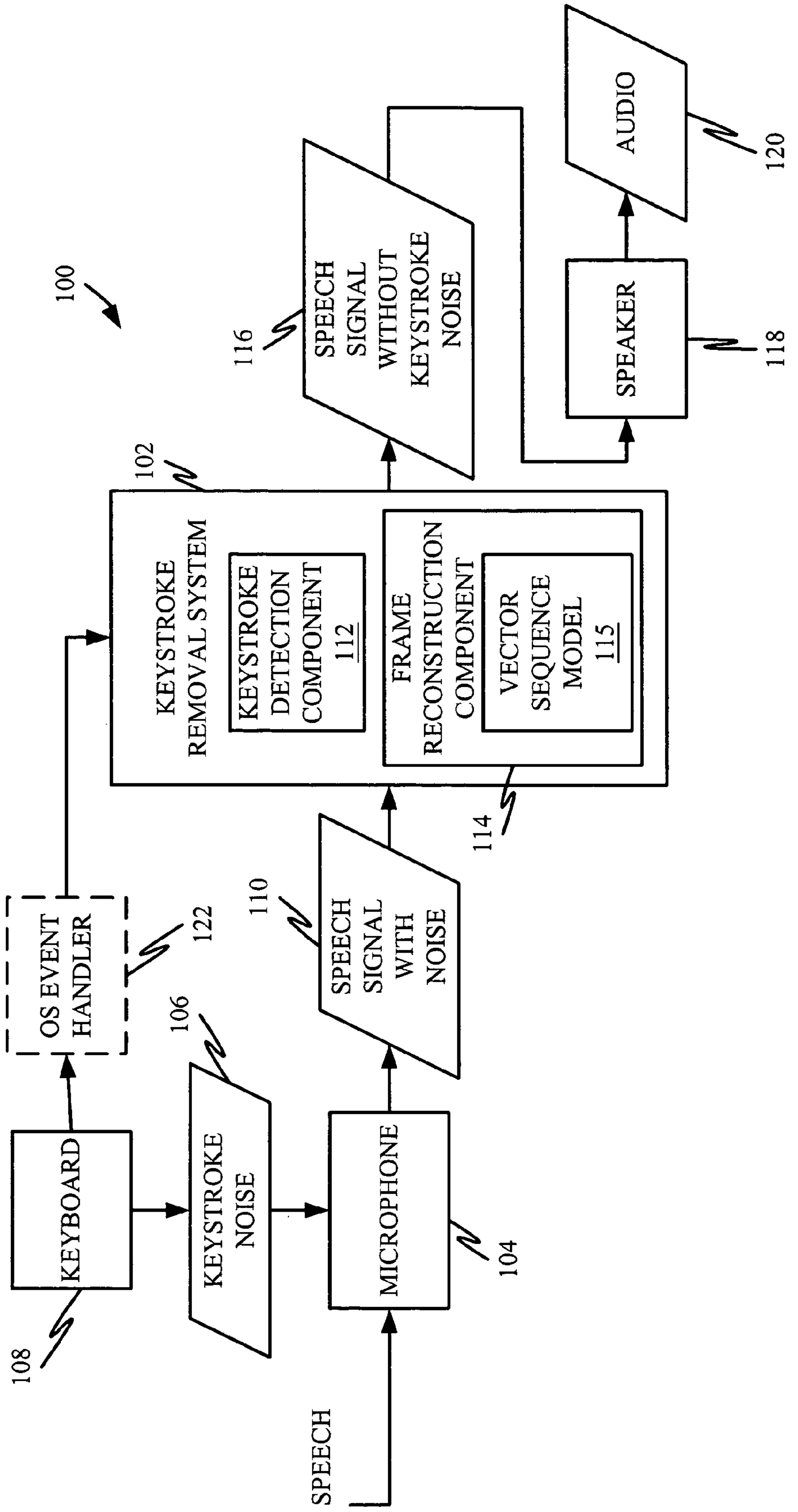
FIG. 1 is a block diagram of one illustrative user input device noise removal system.

FIG. 1 is a block diagram of a speech capture environment 100 which includes a user input device noise removal system 102. System 102 is described herein as a keystroke removal system 102, for the sake of example only. Also, while it will be appreciated that the present system can be used to remove keystroke noise (or noise from other user input devices) from any audio signal, it is described in the context of a speech signal, in this discussion, by way of example only.

Environment 100 includes a user that provides a speech signal to a microphone 104. The microphone also receives keystroke noise 106 from a keyboard 108 that is being used by the user. The microphone 104 therefore provides an audio speech signal 110, with noise, to keystroke removal system 102. Keystroke removal system 102 includes a keystroke detection component 112 and a frame reconstruction component 114 to detect audio frames that are corrupted by keystroke noise, to remove those frames, and to reconstruct the data in those frames to obtain a speech signal 116 without keystroke noise. That signal can then be provided to a speaker 118 to produce audio 120, or it can be provided to any other component (such as a speech recognizer, etc.).

FIG. 1 also shows that environment 100 can illustratively have keystroke removal system 102 coupled to an operating system event handler 122. As will be described later with respect to FIG. 5, operating system event handler 122 indicates when a keystroke down event is detected by the operating system, and when a keystroke up event is detected by the operating system. This information can be provided to keystroke removal system 102 to aid in the detection of keystrokes in the speech signal.

Figure 2:
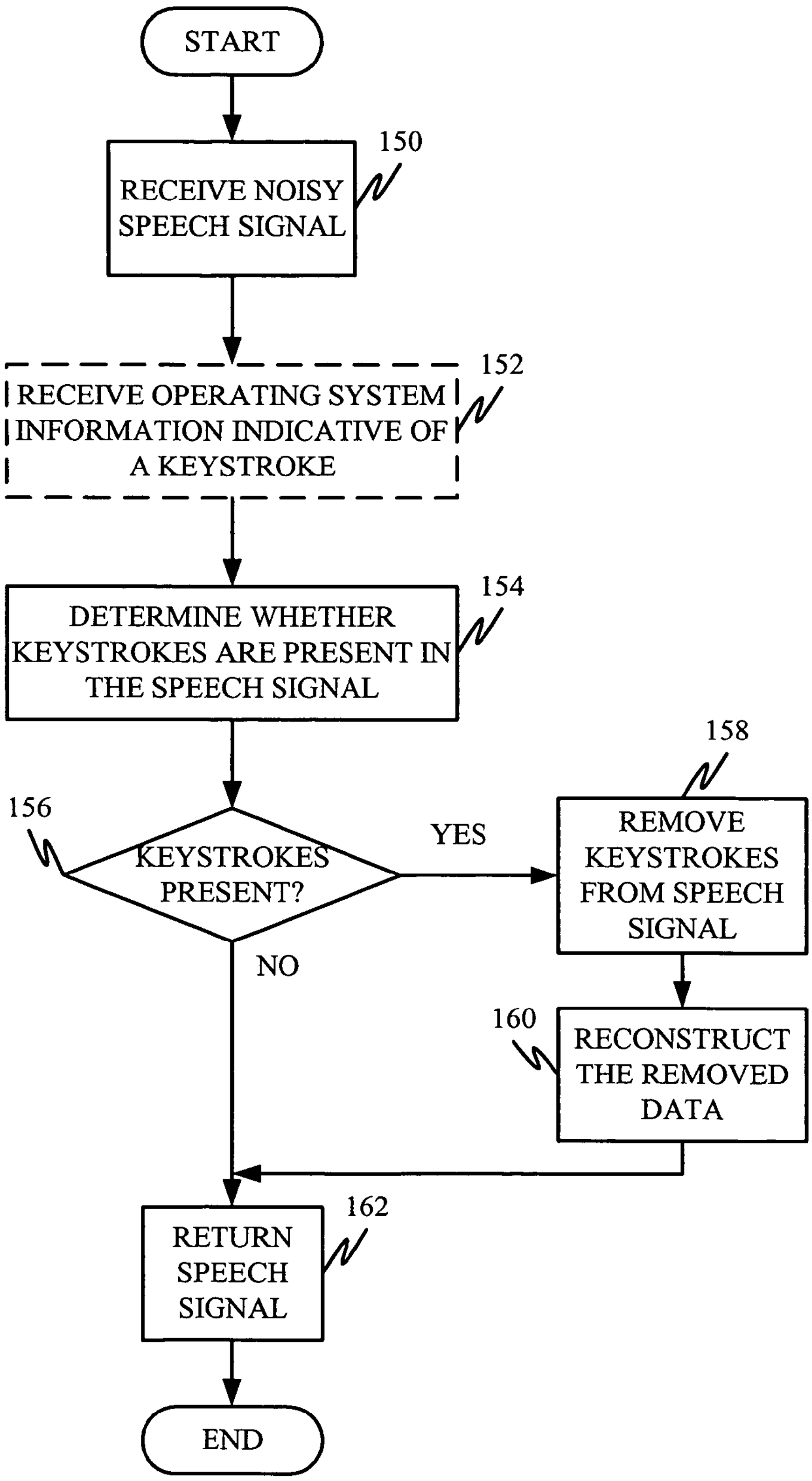
FIG. 2 is a flow diagram illustrating one embodiment of the overall operation of the system shown in FIG. 1.

FIG. 2 is a flow diagram illustrating one embodiment of the overall operation of keystroke removal system 102 shown in FIG. 1. Keystroke removal system 102 first receives the noisy speech signal 100. This is indicated by block 150 in FIG. 2. As is described later with respect to FIG. 5, keystroke removal system 102 can also receive operating system information indicative of a keystroke. This is indicated by the dashed box 152 shown in FIG. 2, and the information is received from operating system event handler 122 shown in FIG. 1.

Keystroke removal system 102 then uses keystroke detection component 112 to determine whether keystrokes are present in the speech signal. This is indicated by block 154 in FIG. 2. If so, the portion of the speech signal corrupted by the keystrokes is removed, and frame reconstruction component 114 is used to reconstruct the removed portion of the speech signal. This is indicated by blocks 156, 158 and 160 in FIG. 2. The clean speech signal 116 is then returned, such as to a speaker 118 or other desired component. This is indicated by block 162 in FIG. 2.

Figure 3:
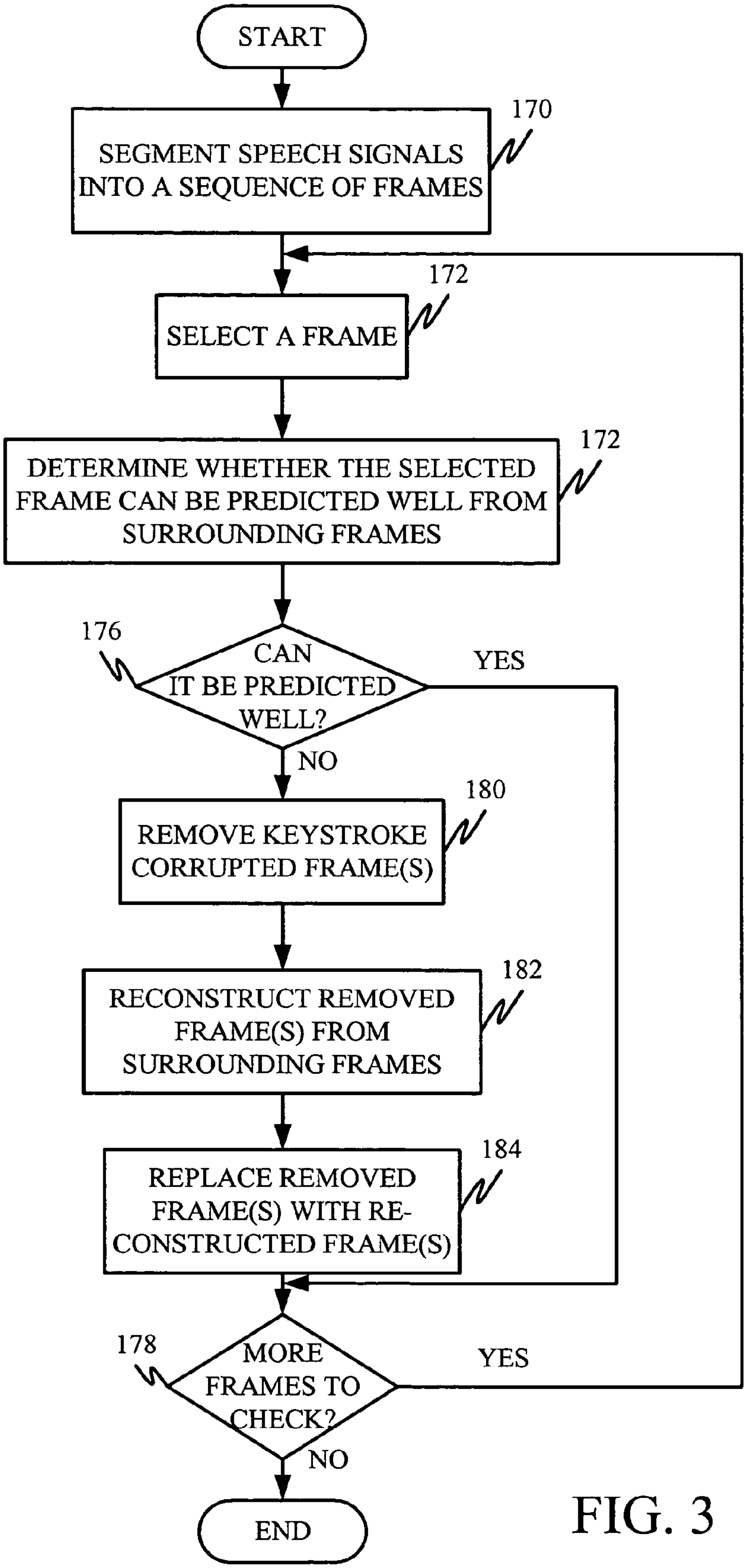
FIG. 3 is a flow diagram illustrating one embodiment of unsupervised keystroke detection.

FIG. 3 is a more detailed block diagram of one embodiment of the operation of keystroke detection component 112 shown in FIG. 1. The embodiment described with respect to FIG. 3 does not include any information from operating system event handler 122. Instead, component 112 is simply implemented as an unsupervised keystroke detection component.

Keystroke removal system 102 receives the speech signal with noise 110 and the speech signal is segmented into a sequence of frames. In one embodiment, the sequence of frames comprises 20-millisecond frames with 10-millisecond overlap with adjacent frames. Segmenting the speech signal into a sequence of frames is indicated by block 170 in FIG. 3.

Next, keystroke detection component 112 selects a frame. This is indicated by block 172. Keystroke detection component 112 then determines whether the selected frame can be predicted well from surrounding frames. This is indicated by block 174. A particular way in which this is done is described in more detail below with respect to FIG. 4.

The reason that the predictability of the selected frame is measured is that speech evolves, in general, quite smoothly and slowly over time. Therefore, any given frame in a speech signal can be predicted relatively accurately from neighboring frames. Therefore, if the selected frame can be predicted accurately from the surrounding frame, it is likely not corrupted by keystroke noise. Therefore, keystroke detection component 112 simply moves to the next frame and determines whether keystroke noise is present in that frame. Determining whether the selected frame can be predicted accurately from surrounding frames and determining whether there are more frames to process is indicated by blocks 176 and 178, respectively, in FIG. 3.

However, if, at block 176, keystroke detection component 112 determines that the selected frame cannot be predicted accurately from the surrounding frames, then the frame is determined to be corrupted with keystroke noise. Because keystroke noise deleteriously affects many, if not all, frequencies components of the corrupted frame, the corrupted frame is simply removed from the speech signal. This is indicated by block 180 in FIG. 3.

Keystroke removal system 102 then uses frame reconstruction component 114 to reconstruct the speech signal for the frames that have been removed. This is indicated by block 182 in FIG. 3. The removed, corrupted frames, are then replaced by the reconstructed frames in the speech signal. This is indicated by block 184 in FIG. 3.

Figure 4:
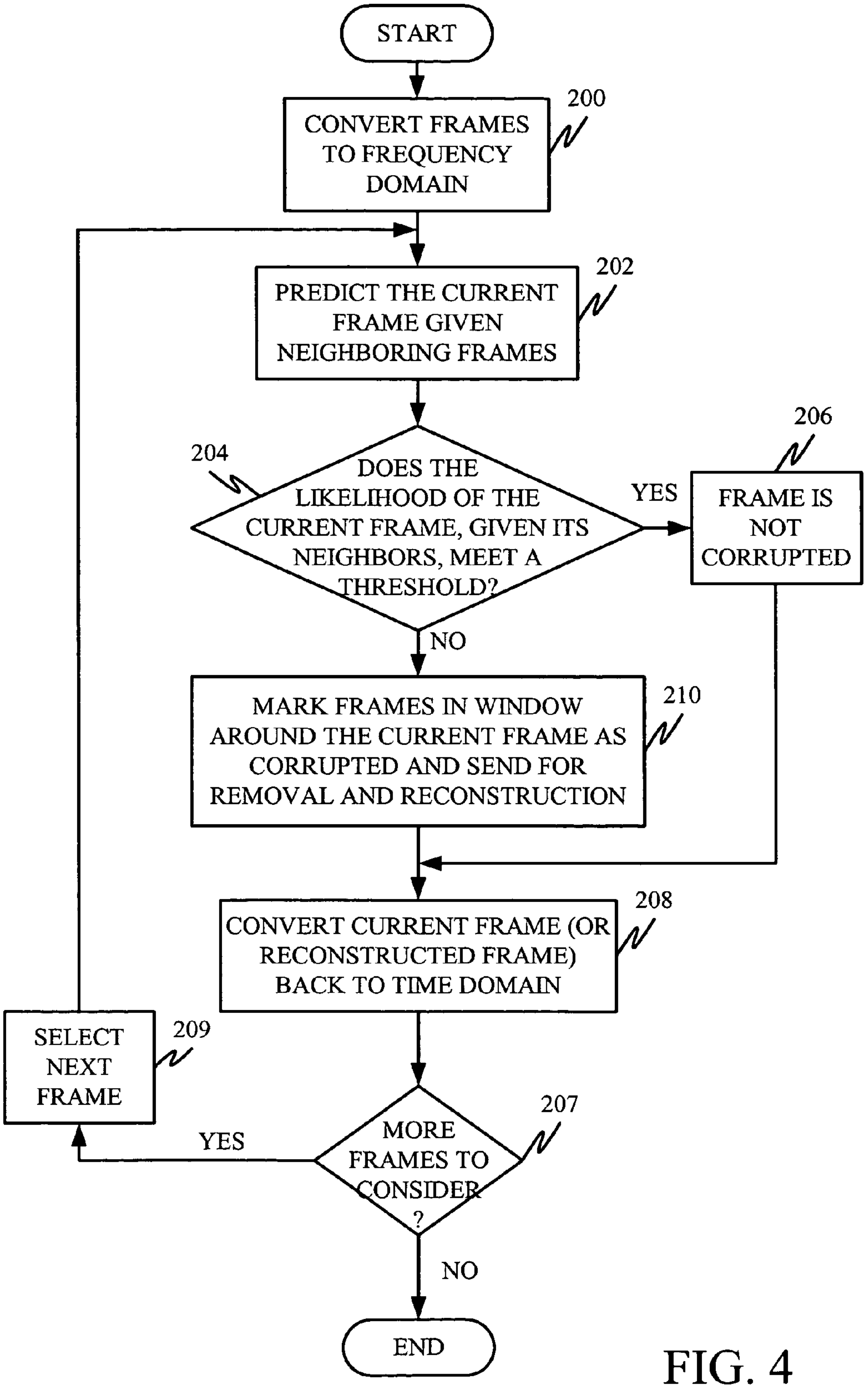
FIG. 4 is a flow diagram illustrating one embodiment in more detail, of how frames corrupted with keystroke noise are identified.

FIG. 4 is a flow diagram better illustrating how keystroke detection component 112 determines whether a selected frame can be predicted, relatively accurately, from its surrounding frames. For purposes of FIG. 4, it is assumed that each speech utterance s(n) is already segmented into frames. Keystroke detection component 112 then converts the frames into the frequency domain. This is indicated by block 200 in FIG. 4. This can be done, for instance, using a Short-Time Fourier Transform (STFT) or any other desired transform. The magnitude of each time-frequency component of the utterance is defined as S(k,t) where t represents the frame index and k represents the spectral index. S(t) represents a vector of all spectral components of frame t. The signal in each spectral subband is assumed to follow a linear predictive model, as follows:

$$S(k,t) = \sum_{m=1}^{M} \alpha_{km} S(k, t-\tau_m) + V(k,t) \qquad \text{Eq. 1}$$

Where $\tau=[\tau_1, \ldots, \tau_M]$ defines the frames used to predict the current frame, $\alpha_k=[\alpha_{k1}, \ldots, \alpha_{kM}]$ are weights applied to these frames, and V(t,k) is zero-mean Gaussian noise (i.e., $V(t,k) \sim \mathcal{N}(0, \sigma_{tk}^2)$)

$\sigma_{tk}^2$ is the variance and $\mathcal{N}(m,v)$ is a Gaussian distribution with mean m and variance v factor. Thus, the following equation can be written:

$$p(S(k,t) \mid S(t, k-\tau_1), \ldots, S(k, t-\tau_M)) = N\left(\sum_{m=1}^{M} \alpha_{jn} S(k, t-\tau_m), \sigma_{tk}^2\right) \qquad \text{Eq. 2}$$

It is assumed that the frequency components in a given frame are independent. Therefore, the joint probability of the frame can be written as:

$$p(S(t)) = \Pi_k p(S(k,t)) \qquad \text{Eq. 3}$$

Therefore, the conditional log-likelihood $F_t$ of the current frame S(t) given the neighboring frames defined by τ can be written as follows:

$$\begin{aligned} F_t &= \log \prod_k p(S(k,t) \mid S(k, t-\tau_1), \ldots, S(k, t-\tau_M)) \\ &= \prod_k \log\{p(S(k,t) \mid S(k, t-\tau_1), \ldots, S(k, t-\tau_M))\} \infty - \\ &\quad \frac{1}{2} \sum_k \frac{1}{\sigma_{tk}^2} \left(S(k,t) - \sum_{m=1}^{M} \alpha_{km} S(k, t-\tau_m)\right)^2 \end{aligned} \qquad \text{Eq. 4}$$

In Eq. 4, $F_t$ measures the likelihood that the signal at frame t can be predicted by the neighboring frames. A threshold value T is then set for $F_t$, and a frame is classified as one that is corrupted by keystroke data if $F_t<T$.

Therefore, referring again to FIG. 4, keystroke detection component 112 predicts a current frame given the neighboring frames. This is done using $F_t$ as set out in Eq. 4 and is indicated by block 202 in FIG. 4.

The value of $F_t$ is then compared to the threshold value T to determine whether the likelihood that the current frame can be predicted from its neighbors meets the threshold value. This is indicated by block 204 in FIG. 4. If the threshold value is met, then keystroke detection component 112 determines that the current frame is not corrupted. This is indicated by block 206. Keystroke removal system 102 then converts the current frame back to the time domain and provides it downstream for further processing (as shown in FIG. 1). This is indicated by block 208 in FIG. 4. Component 112 then determines whether there are more frames to consider. This is indicated by block 207.

However, if, at block 204, it is determined that the present frame cannot be predicted sufficiently accurately given its neighboring frames, then the present frame is marked as one that is corrupted by keystroke data. It has also been empirically noted that keystrokes typically last approximately three frames. Therefore, $\tau$ can be set equal to [−2,2] so that one frame ahead and one frame behind the current frame are also marked as being corrupted by keystroke noise. Marking the frames as being corrupted by keystroke data is indicated by block 210 in FIG. 4. The corrupted frames are sent for reconstruction, then converted back to the time domain as indicated by block 208.

If there are more frames to consider (at block 207) then component 112 selects the next frame for processing. This is indicated by block 209 in FIG. 4.

In addition, the value for the mean can be estimated by setting $\alpha_{km}$=1/m, and the variance in Eq. 1 can be estimated, as follows:

$$\sigma_{tk}^2 = \frac{1}{M}\sum_m (S(k, t-\tau_m))^2 \qquad \text{Eq. 5}$$

Figure 5:
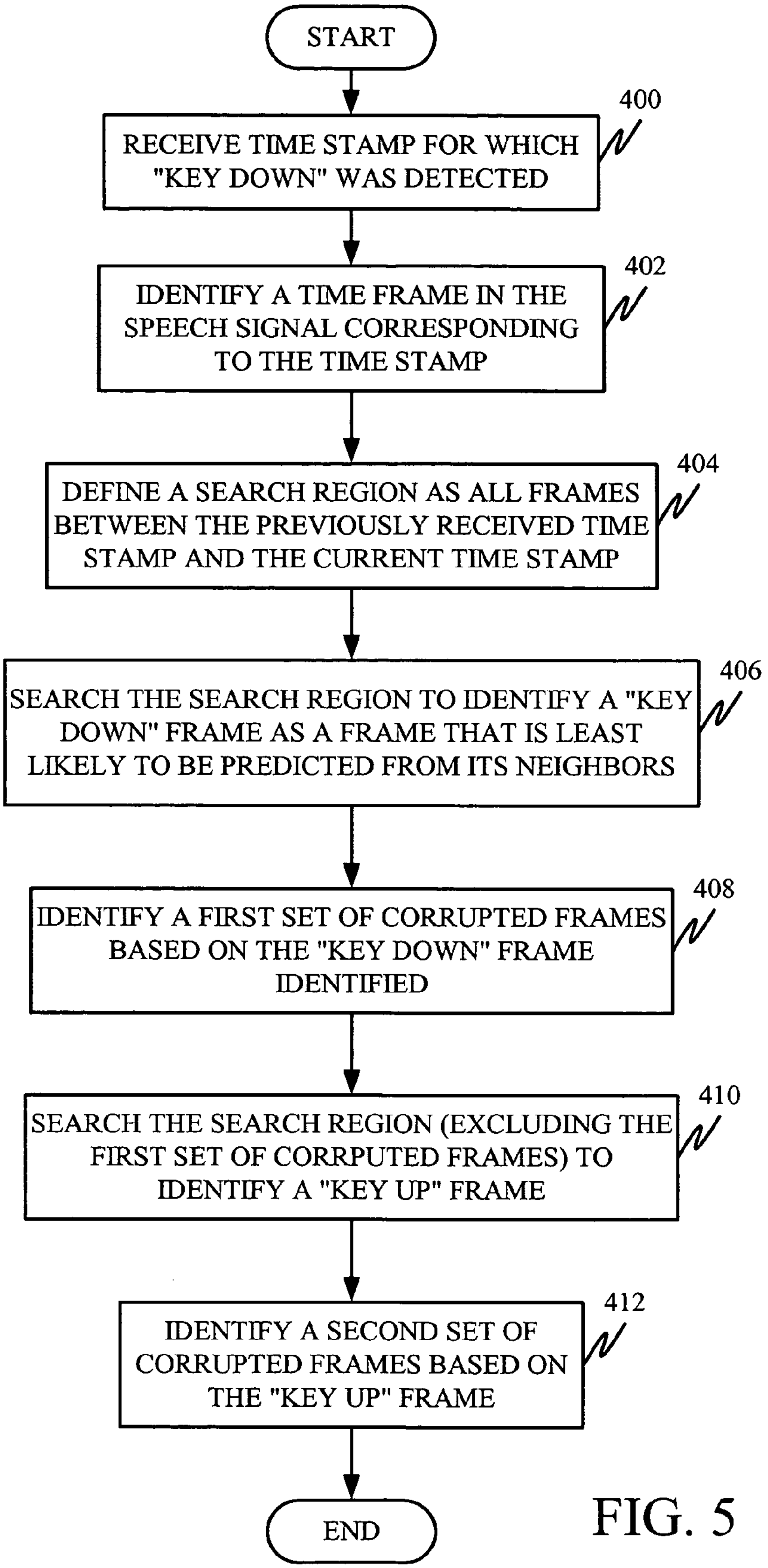
FIG. 5 is a flow diagram of another embodiment for detecting frames corrupted by keystroke noise.

FIG. 5 is a flow diagram illustrating another embodiment of the operation of keystroke detection component 112 shown in FIG. 1. When a key is pressed on keyboard 108 (in FIG. 1) the operating system event handler 122 generates a key down event. Similarly, when a key on keyboard 108 is released, operating system event handler 102 generates a key up event. There is usually a significant delay between the actual physical event and the time that the operating system generates the event. This delay is highly unpredictable and varies with the type of scheduling used by the operating system, the number of active processes, and a variety of other factors.

Despite this, FIG. 5 illustrates a method by which keystroke detection component 112 searches for both the key down and key up events in the speech signal for every key down event received by the operating system event handler 122. Empirically, it has been found that this is more robust than searching for the key down and key up events independently. Therefore, keystroke detection component 112 in keystroke removal system 102 first receives a time frame stamp p corresponding to an associated key down event. This is indicated by block 400 in FIG. 5.

After component 112 receives the time stamp indicating that a key down action was detected by OS event handler 122, component 112 identifies a time frame $t_p$ corresponding to the system clock time p indicated by the time stamp. This is indicated by block 402.

Component 112 then defines a search region $\Theta_p$ as all frames between the previously received time stamp and the current time stamp. In other words, during continuous typing, time stamps corresponding to key down events will be received by component 112. When a current time stamp is received, it is associated with a time frame. Component 112 then knows that the key down action occurred somewhere between the current time frame and the time frame associated with the last time stamp received (which was, itself, associated with a key down action). Therefore, the search region $\Theta_p$ corresponds to all frames between the previous time stamp $t_p-1$ and the current time stamp $t_p$. Defining the search region is indicated by block 404 in FIG. 5.

Component 112 then searches through the search region to identify a key down frame as a frame that is least likely to be predicted from it neighbors. For instance, the function $F_t$ defined above in Eq. 4 predicts how likely a given frame can be predicted from its neighbors. Within the search region defined in step 402, the frame which is least likely to be predicted from its neighbors will be that frame most strongly corrupted by the keystroke within that search region $\Theta_p$. Because the key down action introduces more noise than the key up action, when component 112 finds a local minimum value for $F_t$, within the search region $\Theta_p$, it is very likely that the frame corresponding to that value is the frame which has been corrupted by the key down action. In terms of the mathematical terminology already described, component 112 finds:

$$\hat{t}_D = \underset{t}{\operatorname{argmin}}\{F_t, \forall\, t \in \Theta_p\} \qquad \text{Eq. 6}$$

Identifying the key down frame in the search region is indicated by block 406 in FIG. 5.

Then, because the key down action will corrupt more than one frame, component 112 classifies frames:

$$\Psi_D=\{\hat{t}_D-1, \ldots, \hat{t}_D+l\} \qquad \text{Eq. 7}$$

as keystroke-corrupted frames corresponding to the key down action. Identifying this first set of corrupted frames based on the key down frame is indicated by block 408 in FIG. 5.

Keystroke detection component 112 then finds, within the search region, the frame corresponding to the key up action as follows:

$$\hat{t}_U = \underset{t}{\operatorname{argmin}}\{F_t, \forall\, t \in \Theta_p, t \notin \Psi_D\} \qquad \text{Eq. 8}$$

Identifying the key up frame is indicated by block 410 in FIG. 5.

Component 112 then identifies the set of frames that have been corrupted by the key up action by classifying frames:

$$\Psi_U=\{\hat{t}_U-l, \ldots, t_U+l\} \qquad \text{Eq. 9}$$

as keystroke-corrupted frames corresponding to the key up action. Identifying the second set of corrupted frames based on the key up frame is indicated by block 412 in FIG. 5.

It has been empirically noted that, because key strokes typically last on the order of three frames, setting l=1 provides good performance.

It can be seen that, because component 112 searches the entire search region for the key down and key up frames, it can accurately find those frames, even given significant variability in the lag between the physical occurrence of the keystrokes and the operating system time stamp associated with the keystrokes. It can also be seen, that by using the time stamps from the operating system, component 112 can detect keystrokes in the speech signal without using a threshold T for equation $F_t$.

FIG. 6 is a flow diagram illustrating one illustrative embodiment of the operation of frame reconstruction component 114 (shown in FIG. 1) in removing keystrokes from speech, once the corrupted frames have been located using the detection algorithms implemented by component 112. Some prior systems have used missing feature methods in attempting to deal with keystroke-corrupted speech. However, one difficulty with such methods is determining which spectral components to remove and impute. Because keystrokes are spectrally flat and keystroke-corrupted frames have a low local signal-to-noise ratio due to the proximity of the microphone on the laptop keyboard, it is assumed for the sake of the present discussion that all spectral components of a keystroke-corrupted frame are missing. As described above, this allows the problem of keystroke removal to be recast as one of reconstructing a sequence of frames from its neighbors.

To reconstruct the keystroke-corrupted frames, a correlation-based reconstruction technique is employed in which a sequence of log-spectral vectors of a speech utterance is assumed to be generated by a stationary Gaussian random process. The statistical parameters of this process (its mean and covariance) are estimated from a clean training corpus in order to model the sequence of vectors. The vector sequence model is indicated by block 115 in FIG. 1.

By modeling the sequence of vectors in this manner, covariances are estimated not just across frequency, but across time as well. Because the process is assumed to be stationary, the estimated mean vector is independent of time and the covariance between any two components is only a function of the time difference between them.

In order for the data to better fit the Gaussian assumption of model 115, operations are performed on the log-magnitude spectra rather than on the magnitude directly.

Thus, frame reconstruction component 114 first receives the frames marked as corrupted (from component 112) and the neighboring frames of the corrupted frames. This is indicated by block 500 in FIG. 6. Frame reconstruction component 114 then removes the corrupted frames, as indicated by block 510. The magnitude and phase of the neighboring (clean) frames are then separated, and the log magnitude is calculated as follows:

$$X(t)=\log(S(t)) \qquad \text{Eq. 10}$$

where S(t) represents the magnitude spectrum as discussed above. The log magnitude vectors for the clean (observed) and the keystroke-corrupted (missing) speech are defined as $X_0$ and $X_m$, respectively. Separating the magnitude and phase of the clean frames is indicated by block 512 in FIG. 6.

Under the Gaussian process assumption, a MAP estimate of $X_m$ can now be expressed as follows:

$$\hat{X}_m(t) = E[X_m \mid X_o(t)] = \mu_m + \sum_{mo}\sum_{\infty}^{-1}(X_o(t)-\mu_o) \qquad \text{Eq. 11}$$

where $$\sum_{mo}\sum_{oo}$$

are the appropriate partitions of the covariance matrix learned in training. Thus, for each keystroke-corrupted frame in:

$$\Psi=\{\Psi_D,\Psi_U\}, \qquad \text{Eq. 12}$$

frame reconstruction component 114 sets the log magnitude vectors as follows:

$$\text{Set}\begin{cases} X_m(t) = \left[X(\hat{t}_D - l)^T \ldots X(\hat{t}_D + l)^T\right]^T \\ X_o(t) = \left[X(\hat{t}_D - l - 1)^T X(\hat{t}_D + l + 1)^T\right]^T \end{cases} \qquad \text{Eq. 13}$$

Component 114 then estimates the magnitude spectrum for the missing frames using model 115 and the observed values in the neighboring frames according to Eq. 11, set out above. Estimating the magnitude spectrum for the missing frames is indicated by block 514 in FIG. 6. Of course, for each keystroke-corrupted frame, the steps of setting the log magnitude vectors and computing the map estimate according to Eq. 11 are repeated.

Finally, the estimated magnitude spectrum is recombined with the phase for the missing frames, to fully reconstruct the frames. This is indicated by block 516 in FIG. 6

FIG. 6A is a more detailed portion of the flow diagram shown in FIG. 6, for estimating the magnitude spectrum for the missing frames as in block 514. By imposing locality constraints on both the mean and covariance in the Gaussian model 115 that is used, the computational expense in performing the matrix operations is reduced, because the dimensionality of the vectors represented by the matrices is reduced. Therefore, frame reconstruction component 114 computes the estimate of the magnitude spectrum for the missing frames preserving only local correlations in the covariance matrix. This is indicated by block 518 in FIG. 6.

In other words, in the log spectral domain, each frame consists of N components, where 2N is the DFT size. Conversely, $$\sum_{\infty}$$

is cN×cN, where c is the number of frames of observed speech used to estimate the missing frames. Typically, $N \geqq 128$ and $c \geqq 2$, making the matrix inversion required in Eq. 11 computationally expensive. To reduce the complexity of the operations, it is assumed that the covariance matrix has a block-diagonal structure, preserving only local correlations. If a block size B is used, then the inverse of N/B matrices of size cB×cB is computed, thus reducing the number of computations. In one embodiment, B was empirically set to 5, although other values of B can be used as well.

Using a block diagonal covariance structure also improves the environmental robustness of farfield speech. There can be long-span correlations across time and frequency in close-talking speech. However, these correlations can be significantly weaker in farfield audio. This mismatch results in reconstruction errors, producing artifacts in the resulting audio. By using a block-diagonal structure, only short-span correlations are utilized, making the reconstruction more robust in unseen farfield conditions. To incorporate this change into the MAP estimation algorithm, the single MAP estimation for the keystroke-corrupted frames is simply replaced with multiple estimations, one for each block in the covariance matrix.

Also, in order to reduce the complexity of the computations performed, component 114 illustratively performs the estimation of the magnitude spectrum for the missing frames by estimating a locally adapted mean vector. This is indicated by block 520 in FIG. 6.

In other words, the Gaussian model 115 described above with respect to Eq. 11 uses a single mean vector to represent all speech. Because the present system illustratively reconstructs the full magnitude spectrum of the missing frames, and because it operates on farfield audio, there is considerable variation in the observed features. This can result, when using a single pre-trained mean vector in the MAP estimation process, in some reconstruction artifacts.

In one embodiment, a single mean vector is still used, but it is used with a locally adapted value. To locally adapt the mean vector value, a linear predictive framework, similar to that discussed above in Eq. 4 for detecting corrupted frames, can be used. The mean vector is estimated as a linear combination of the neighboring clean frame surrounding the keystroke-corrupted segment of the signal. Assume that $\mu_k$ is the kth spectral component of the mean vector $\mu$, then the adapted value of this component can be defined as follows:

$$\hat{\mu}_k = \sum_{\tau \in \Gamma} \beta_\tau X(t-\tau, k) \quad \text{Eq. 14}$$

Where $\Gamma$ defines the indices of the neighboring clean frames, and $\beta_\tau$ is the weight applied to the observation at time $t-\tau$. Because the mean is computed online, it can easily adapt to different environmental conditions. In one embodiment, the adapted mean value in Eq. 14 is estimated as the same mean of the frames used for reconstruction, by setting $\Gamma$ to the indices of frames in $X_0$ and $\beta_\tau 1/|\Gamma|$.

It should be also noted that the present discussion has proceeded by removing the entire spectral content of corrupted frames. However, where only specific portions of the spectral content of a corrupted frame are corrupted, only the corrupt spectral content needs to be removed. The uncorrupt portions can then be used to estimate the corrupt portions along with reliable surrounding frames. The estimation is the same as that described above except that the definition of $X_m$ and $X_0$ would, of course, change slightly to reflect that only a portion of the spectral content is being estimated.

Figure 7:
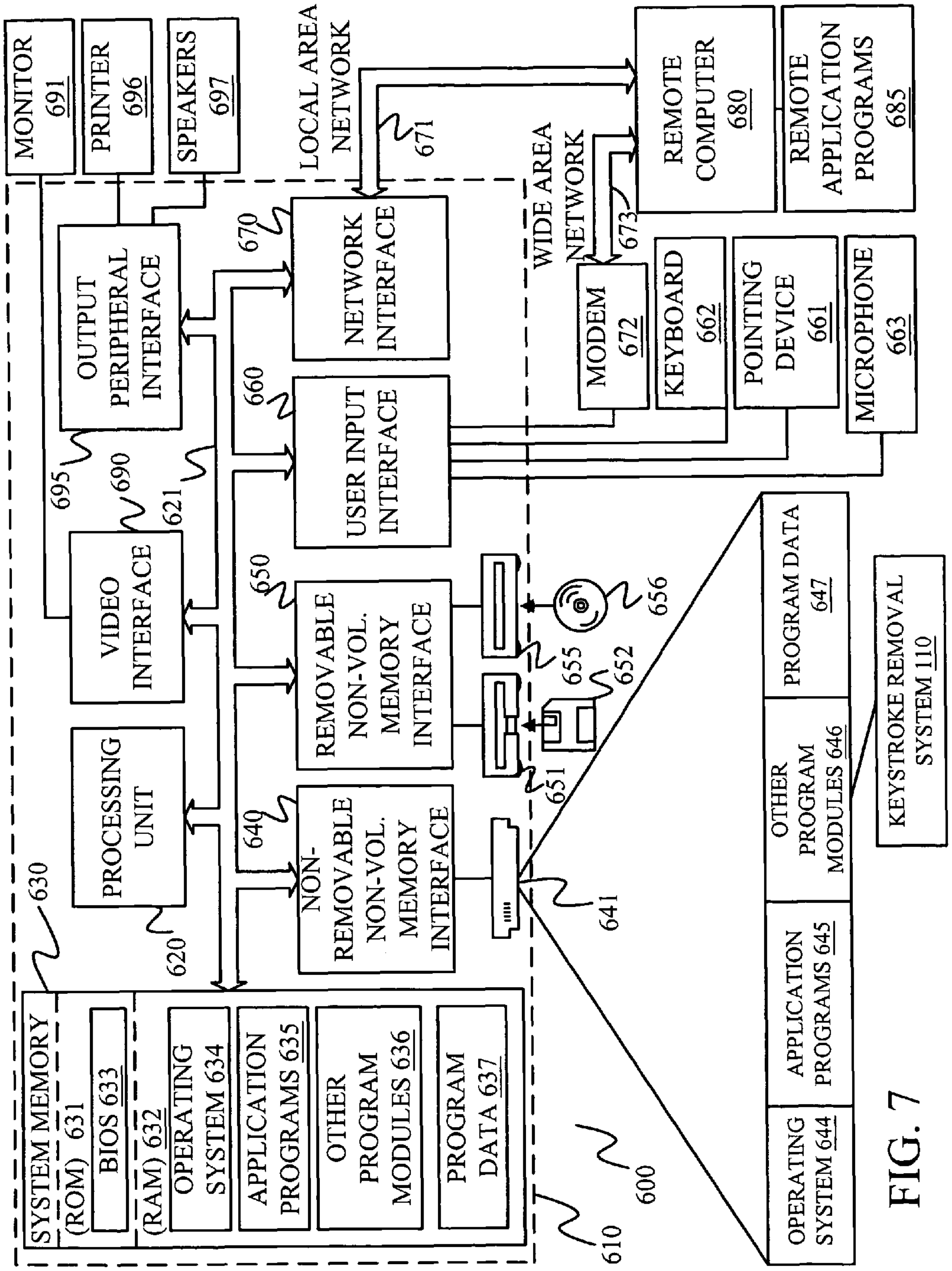
FIG. 7 is a block diagram of one illustrative computing environment in which the present system can be used.

FIG. 7 illustrates an example of a suitable computing system environment 600 on which embodiments may be implemented. The computing system environment 600 is only one example of a suitable computing environment and is not intended to suggest any limitation as to the scope of use or functionality of the claimed subject matter. Neither should the computing environment 600 be interpreted as having any dependency or requirement relating to any one or combination of components illustrated in the exemplary operating environment 600.

Embodiments are operational with numerous other general purpose or special purpose computing system environments or configurations. Examples of well-known computing systems, environments, and/or configurations that may be suitable for use with various embodiments include, but are not limited to, personal computers, server computers, hand-held or laptop devices, multiprocessor systems, microprocessor-based systems, set top boxes, programmable consumer electronics, network PCs, minicomputers, mainframe computers, telephony systems, distributed computing environments that include any of the above systems or devices, and the like.

Embodiments may be described in the general context of computer-executable instructions, such as program modules, being executed by a computer. Generally, program modules include routines, programs, objects, components, data structures, etc. that perform particular tasks or implement particular abstract data types. Some embodiments are designed to be practiced in distributed computing environments where tasks are performed by remote processing devices that are linked through a communications network. In a distributed computing environment, program modules are located in both local and remote computer storage media including memory storage devices.

With reference to FIG. 7, an exemplary system for implementing some embodiments includes a general-purpose computing device in the form of a computer 610. Components of computer 610 may include, but are not limited to, a processing unit 620, a system memory 630, and a system bus 621 that couples various system components including the system memory to the processing unit 620. The system bus 621 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 610 typically includes a variety of computer readable media. Computer readable media can be any available media that can be accessed by computer 610 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 610. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 630 includes computer storage media in the form of volatile and/or nonvolatile memory such as read only memory (ROM) 631 and random access memory (RAM) 632. A basic input/output system 633 (BIOS), containing the basic routines that help to transfer information between elements within computer 610, such as during start-up, is typically stored in ROM 631. RAM 632 typically contains data and/or program modules that are immediately accessible to and/or presently being operated on by processing unit 620. By way of example, and not limitation, FIG. 7 illustrates operating system 634, application programs 635, other program modules 636, and program data 637.

The computer 610 may also include other removable/non-removable volatile/nonvolatile computer storage media. By way of example only, FIG. 7 illustrates a hard disk drive 641 that reads from or writes to non-removable, nonvolatile magnetic media, a magnetic disk drive 651 that reads from or writes to a removable, nonvolatile magnetic disk 652, and an optical disk drive 655 that reads from or writes to a removable, nonvolatile optical disk 656 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 641 is typically connected to the system bus 621 through a non-removable memory interface such as interface 640, and magnetic disk drive 651 and optical disk drive 655 are typically connected to the system bus 621 by a removable memory interface, such as interface 650.

The drives and their associated computer storage media discussed above and illustrated in FIG. 7, provide storage of computer readable instructions, data structures, program modules and other data for the computer 610. In FIG. 7, for example, hard disk drive 641 is illustrated as storing operating system 644, application programs 645, other program modules 646, and program data 647. Note that these components can either be the same as or different from operating system 634, application programs 635, other program modules 636, and program data 637. Operating system 644, application programs 645, other program modules 646, and program data 647 are given different numbers here to illustrate that, at a minimum, they are different copies. FIG. 7 shows that, in one embodiment, system 110 resides in other program modules 646. Of course, it could reside other places as well, such as in remote computer 680, or elsewhere.

A user may enter commands and information into the computer 610 through input devices such as a keyboard 662, a microphone 663, and a pointing device 661, such as a mouse, trackball or touch pad. Other input devices (not shown) may include a joystick, game pad, satellite dish, scanner, or the like. These and other input devices are often connected to the processing unit 620 through a user input interface 660 that is coupled to the system bus, but may be connected by other interface and bus structures, such as a parallel port, game port or a universal serial bus (USB). A monitor 691 or other type of display device is also connected to the system bus 621 via an interface, such as a video interface 690. In addition to the monitor, computers may also include other peripheral output devices such as speakers 697 and printer 696, which may be connected through an output peripheral interface 695.

The computer 610 is operated in a networked environment using logical connections to one or more remote computers, such as a remote computer 680. The remote computer 680 may be a personal computer, a hand-held device, a server, a router, a network PC, a peer device or other common network node, and typically includes many or all of the elements described above relative to the computer 610. The logical connections depicted in FIG. 7 include a local area network (LAN) 671 and a wide area network (WAN) 673, but may also include other networks. Such networking environments are commonplace in offices, enterprise-wide computer networks, intranets and the Internet.

When used in a LAN networking environment, the computer 610 is connected to the LAN 671 through a network interface or adapter 670. When used in a WAN networking environment, the computer 610 typically includes a modem 672 or other means for establishing communications over the WAN 673, such as the Internet. The modem 672, which may be internal or external, may be connected to the system bus 621 via the user input interface 660, or other appropriate mechanism. In a networked environment, program modules depicted relative to the computer 610, or portions thereof, may be stored in the remote memory storage device. By way of example, and not limitation, FIG. 7 illustrates remote application programs 685 as residing on remote computer 680. It will be appreciated that the network connections shown are exemplary and other means of establishing a communications link between the computers may be used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method of removing user input device noise from an audio signal, comprising:

receiving a corrupted audio signal including user input device noise from user inputs on a user input device, wherein the user input device noise comprises noise generated during the user inputs as a result of physical interactions with the user input device;

dividing the corrupted audio signal into frames;

identifying a set of frames corrupted by the user input device noise, wherein identifying a set of frames comprises:

identifying a search space based on an operating system time stamp associated with a frame in the audio signal;

searching the search space for a first frame that is least similar to neighboring frames;

identifying a first set of frames as corrupted frames based on the first frame that is least similar; and removing corrupted spectral content of the set of identified frames; and reconstructing the corrupted spectral content of the set of identified frames, without the user input device noise, from neighboring frames proximate the set of identified frames.

2. The method of claim 1 wherein removing corrupted spectral content comprises:

removing an entire spectral content of the set of identified frames.

3. The method of claim 1 wherein identifying a set of frames corrupted by the user input device noise, comprises:

calculating how well a selected frame can be predicted based on surrounding frames, in the audio signal; and identifying whether the selected frame is corrupted by user input device noise based on the step of calculating.

4. The method of claim 3 wherein identifying a set of frames comprises:

if the selected frame is corrupted by the user input device noise, identifying the set of frames as the selected frame and one or more additional frames, closely proximate the selected frame in the audio signal.

5. The method of claim 4 wherein the one or more additional frames include one or more frames immediately preceding the selected frame and one or more frames immediately following the selected frame.

6. The method of claim 3 wherein calculating comprises:

calculating a similarity of the selected frame to given other frames, closely proximate the selected frame in the audio signal.

7. The method of claim 3 wherein identifying comprises:

determining that the selected frame is corrupted by user input device noise if the similarity fails to meet a predetermined threshold.

8. The method of claim 1 wherein identifying a set of frames further comprises:

searching the search space for a second frame, not in the first set of frames, that is least similar to neighboring frames; and identifying a second set of frames as corrupted frames based on the second frame.

9. The method of claim 1 wherein identifying a search space comprises:

identifying the search space as extending in the audio signal from the frame associated with the time stamp to a frame associated with an immediately preceding time stamp.

10. The method of claim 1 wherein reconstructing, comprises:

reconstructing the magnitude of the corrupted spectral content of the set of identified frames.

11. A method of reconstructing an audio signal corrupted by user input device noise, comprising:

removing a corrupted spectral content of a set of frames in the audio signal corrupted by the user input device noise;

estimating clean values for the corrupted spectral content removed based on observed values in neighboring frames, neighboring the set of frames, wherein estimating comprises estimating the clean values based on a model of correlation between vector values in a sequence of vectors of log spectra from a training corpus;

combining the estimated clean values of the spectral content with a phase of the audio signal to obtain a combined audio signal; and outputting the combined audio signal.

12. The method of claim 11 wherein the model includes mean and covariance parameters, the mean and covariance parameters having imposed locality constraints.

13. A system for removing user input device noise from an audio signal, comprising:

a noise detection device configured to identify a portion of the audio signal that includes user input device noise, wherein the noise detection device is configured to identify the portion of the audio signal by calculating how likely a selected portion of the audio signal is, given surrounding portions of the audio signal, and wherein the user input device noise comprises noise generated during user inputs as a result of physical interactions with a user input device, the noise detection device including an input detection device configured to receive a time stamp indicative of a time of occurrence of one of the user interactions in a computer system; and a signal reconstruction device configured to remove magnitude values of a spectral content of the portion of the audio signal and to estimate clean magnitude values based on values proximate the removed values in the audio signal.

14. The system of claim 13 wherein the signal reconstruction device comprises:

a vector sequence model trained to model clean sequences of spectral vectors and correlations between values in the spectral vectors.

15. The system of claim 13 wherein the input detection device is configured to identify a first portion of the audio signal corrupted by the user input noise from an input device actuation event based on the time stamp.

16. The system of claim 15 wherein the input detection device is configured to identify a second portion of the audio signal corrupted by the user input noise from a release of the input device actuation event based on the time stamp.

17. A system for removing user input device noise from an audio signal, comprising:

an signal receiving device that receives a corrupted audio signal that includes user input device noise from user inputs on a user input device, wherein the user input device noise comprises noise generated during the user inputs as a result of physical interactions with the user input device; a signal dividing device that divides the corrupted audio signal into frames;

a frame identification device that identifies a set of frames corrupted by the user input device noise, wherein identifying a set of frames comprises; identifying a search space based on an operating system time stamp associated with a frame in the audio signal;

searching the search space for a first frame that is least similar to neighboring frames;

identifying a first set of frames as corrupted frames based on the first frame that is least similar; and a content removal device that removes corrupted spectral content of the set of identified frames; and a signal reconstruction device that reconstructs the corrupted spectral content of the set of identified frames, without the user input device noise, from neighboring frames proximate the set of identified frames.

18. A system for reconstructing an audio signal corrupted by user input device noise, comprising:

a signal removal device that removes a corrupted spectral content of a set of frames in the audio signal corrupted by the user input device noise; an estimation device that estimates clean values for the corrupted spectral content removed based on observed values in neighboring frames, neighboring the set of frames, wherein estimating comprises estimating the clean values based on a model of correlation between vector values in a sequence of vectors of log spectra from a training corpus;

an estimation combining device that combines the estimated clean values of the spectral content with a phase of the audio signal to obtain a combined audio signal; and an output device that outputs the combined audio signal.

19. A method for removing user input device noise from an audio signal, comprising:

identifying a portion of the audio signal that includes user input device noise, wherein identifying comprises identifying the portion of the audio signal by calculating how likely a selected portion of the audio signal is, given surrounding portions of the audio signal, and wherein the user input device noise comprises noise generated during user inputs as a result of physical interactions with a user input device, and wherein identifying still further comprises receiving a time stamp indicative of a time of occurrence of one of the user interactions, in a computer system; and removing magnitude values of a spectral content of the portion of the audio signal and estimating clean magnitude values based on values proximate the removed values in the audio signal.

* * * * *